(12) United States Patent
Theimer

(10) Patent No.: US 9,521,505 B2
(45) Date of Patent: *Dec. 13, 2016

(54) MOBILE TELEPHONE FOR INTERNET APPLICATIONS

(71) Applicant: Nokia Technologies Oy, Espoo (FI)

(72) Inventor: Wolfgang Theimer, Bochum (DE)

(73) Assignee: NOKIA TECHNOLOGIES OY, Espoo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 15/214,002

(22) Filed: Jul. 19, 2016

(65) Prior Publication Data

US 2016/0330568 A1    Nov. 10, 2016

Related U.S. Application Data

(60) Continuation of application No. 14/622,187, filed on Feb. 13, 2015, now Pat. No. 9,420,402, which is a continuation of application No. 12/851,780, filed on Aug. 6, 2010, now Pat. No. 8,995,316, which is a continuation of application No. 11/411,263, filed on Apr. 26, 2006, now abandoned, which is a division of application No. 10/309,544, filed on Dec. 4, 2002, now Pat. No. 7,061,897, which is a continuation of (Continued)

(30) Foreign Application Priority Data

Oct. 15, 1997   (DE) .................................. 197 45 539

(51) Int. Cl.
  *H04L 29/08*   (2006.01)
  *H04W 4/00*    (2009.01)
  *H04M 1/725*   (2006.01)

(52) U.S. Cl.
  CPC .............. *H04W 4/003* (2013.01); *H04L 67/02* (2013.01); *H04L 67/12* (2013.01); *H04L 67/18* (2013.01); *H04M 1/72561* (2013.01)

(58) Field of Classification Search
  CPC .... H04W 4/003; H04M 1/72561; G06F 21/33
  See application file for complete search history.

(56) References Cited

U.S. PATENT DOCUMENTS

| | | |
|---|---|---|
| 4,803,625 A | 2/1989 | Fu et al. |
| 5,263,178 A | 11/1993 | Liukkonen |
| 5,353,328 A | 10/1994 | Jokimies |

(Continued)

FOREIGN PATENT DOCUMENTS

| | | |
|---|---|---|
| CA | 2218169 A1 | 8/1997 |
| DE | 19603483 A1 | 9/1996 |

(Continued)

OTHER PUBLICATIONS

Poyhonen, "GSM PLMN Makes a Mobile Office Viable", pp. 375-378.

(Continued)

*Primary Examiner* — Wei Zhao
(74) *Attorney, Agent, or Firm* — Ditthavong & Steiner, P.C.

(57) ABSTRACT

A control unit for a mobile telephone includes a Web server adapted to connect to a Web browser in the mobile telephone, wherein the Web server receives information and provides the information to the Web browser when connected to the Web browser.

22 Claims, 4 Drawing Sheets

Related U.S. Application Data application No. 09/172,547, filed on Oct. 14, 1998, now Pat. No. 6,519,241.

(56) References Cited

U.S. PATENT DOCUMENTS

| | | | |
|---|---|---|---|
| 5,392,282 A | 2/1995 | Kiema | |
| 5,490,235 A | 2/1996 | Von Holten et al. | |
| 5,515,043 A | 5/1996 | Berard et al. | |
| 5,537,608 A | 7/1996 | Beatty et al. | |
| 5,544,661 A | 8/1996 | Davis et al. | |
| 5,619,684 A | 4/1997 | Goodwin et al. | |
| 5,682,525 A | 10/1997 | Bouve et al. | |
| 5,727,159 A | 3/1998 | Kikinis | |
| 5,732,074 A | 3/1998 | Spaur et al. | |
| 5,752,976 A | 5/1998 | Duffin et al. | |
| 5,772,586 A | 6/1998 | Heinonen et al. | |
| 5,802,351 A | 9/1998 | Frampton | |
| 5,809,415 A | 9/1998 | Rossmann | |
| 5,852,777 A | 12/1998 | Harrison | |
| 5,857,967 A | 1/1999 | Frid et al. | |
| 5,872,915 A * | 2/1999 | Dykes | G06F 21/41 726/5 |
| 5,905,957 A | 5/1999 | Olds | |
| 5,907,023 A | 5/1999 | Chawla | |
| 5,926,116 A | 7/1999 | Kitano et al. | |
| 5,926,624 A | 7/1999 | Katz et al. | |
| 5,948,066 A | 9/1999 | Whalen et al. | |
| 5,953,392 A | 9/1999 | Rhie et al. | |
| 5,956,487 A | 9/1999 | Venkatraman et al. | |
| 5,958,016 A | 9/1999 | Chang et al. | |
| 5,974,447 A | 10/1999 | Cannon et al. | |
| 5,997,476 A | 12/1999 | Brown | |
| 6,018,710 A | 1/2000 | Wynblatt et al. | |
| 6,022,315 A | 2/2000 | Iliff | |
| 6,028,917 A | 2/2000 | Creamer et al. | |
| 6,044,382 A | 3/2000 | Martino | |
| 6,049,769 A | 4/2000 | Holmes et al. | |
| 6,049,796 A | 4/2000 | Siitonen et al. | |
| 6,052,785 A | 4/2000 | Lin et al. | |
| 6,055,506 A | 4/2000 | Frasca, Jr. | |
| 6,070,184 A * | 5/2000 | Blount | H04L 29/06 709/200 |
| 6,076,099 A | 6/2000 | Chen et al. | |
| 6,088,746 A | 7/2000 | Koppa | |
| 6,112,078 A | 8/2000 | Sormunen et al. | |
| 6,112,099 A | 8/2000 | Ketola | |
| 6,115,611 A | 9/2000 | Kimoto et al. | |
| 6,119,167 A | 9/2000 | Boyle et al. | |
| 6,125,384 A | 9/2000 | Brandt et al. | |
| 6,131,040 A | 10/2000 | Knuutila et al. | |
| 6,148,253 A | 11/2000 | Taguchi et al. | |
| 6,151,355 A | 11/2000 | Vallee et al. | |
| 6,154,745 A | 11/2000 | Kari et al. | |
| 6,169,897 B1 | 1/2001 | Kariya | |
| 6,170,007 B1 | 1/2001 | Venkatraman et al. | |
| 6,195,546 B1 | 2/2001 | Leung et al. | |
| 6,195,564 B1 | 2/2001 | Rydbeck et al. | |
| 6,209,026 B1 | 3/2001 | Ran et al. | |
| 6,219,696 B1 | 4/2001 | Wynblatt et al. | |
| 6,226,523 B1 | 5/2001 | Karlsson et al. | |
| 6,236,365 B1 | 5/2001 | LeBlanc et al. | |
| 6,256,498 B1 | 7/2001 | Ludwig | |
| 6,282,454 B1 | 8/2001 | Papadopoulos et al. | |
| 6,292,668 B1 | 9/2001 | Alanara et al. | |
| 6,292,858 B1 | 9/2001 | Inkinen | |
| 6,301,590 B1 | 10/2001 | Siow et al. | |
| 6,332,086 B2 | 12/2001 | Avis | |
| 6,338,096 B1 | 1/2002 | Ukelson | |
| 6,353,743 B1 | 3/2002 | Karmel | |
| 6,370,591 B2 | 4/2002 | Kaihlaniemi | |
| 6,381,535 B1 | 4/2002 | Durocher | |
| 6,393,014 B1 | 5/2002 | Daly et al. | |
| 6,405,049 B2 | 6/2002 | Herrod et al. | |
| 6,430,409 B1 | 8/2002 | Rossmann | |
| 6,466,783 B2 | 10/2002 | Dahm et al. | |
| 6,473,609 B1 | 10/2002 | Schwartz et al. | |
| 6,496,704 B2 | 12/2002 | Yuan | |
| 6,507,864 B1 | 1/2003 | Klein et al. | |
| 6,519,241 B1 | 2/2003 | Theimer | |
| 6,529,159 B1 | 3/2003 | Fan et al. | |
| 6,558,321 B1 | 5/2003 | Burd et al. | |
| 6,579,231 B1 | 6/2003 | Phipps | |
| 6,587,450 B1 | 7/2003 | Pasanen | |
| 6,615,267 B1 | 9/2003 | Whalen et al. | |
| 6,625,447 B1 | 9/2003 | Rossmann | |
| 6,629,642 B1 | 10/2003 | Swartz et al. | |
| 6,636,502 B1 | 10/2003 | Lager et al. | |
| 6,714,969 B1 | 3/2004 | Klein et al. | |
| 6,747,692 B2 | 6/2004 | Patel et al. | |
| 6,789,102 B2 | 9/2004 | Gotou et al. | |
| 6,920,637 B2 | 7/2005 | Mason et al. | |
| 6,996,609 B2 | 2/2006 | Hickman et al. | |
| 7,003,284 B2 | 2/2006 | Schwartz et al. | |
| 7,032,001 B1 | 4/2006 | Herrod et al. | |
| 7,061,897 B2 | 6/2006 | Theimer | |
| 7,225,249 B1 | 5/2007 | Barry et al. | |
| 7,325,077 B1 | 1/2008 | Nguyen | |
| 7,502,656 B2 | 3/2009 | Thibault et al. | |
| 7,624,028 B1 | 11/2009 | Brown | |
| 7,734,305 B2 | 6/2010 | Alanara et al. | |
| 8,229,485 B2 | 7/2012 | Alanara et al. | |
| 8,620,685 B2 | 12/2013 | Brown | |
| 9,420,402 B2 * | 8/2016 | Theimer | G06F 21/33 |
| 2001/0041535 A1 | 11/2001 | Karmel | |
| 2001/0055978 A1 | 12/2001 | Herrod et al. | |
| 2003/0076792 A1 | 4/2003 | Theimer | |
| 2008/0015937 A1 | 1/2008 | Perkowski et al. | |
| 2010/0138557 A1 | 6/2010 | Mason et al. | |

FOREIGN PATENT DOCUMENTS

| | | |
|---|---|---|
| DE | 19713538 A1 | 8/1997 |
| DE | 69735526 T2 | 8/2006 |
| EP | 0251520 A2 | 1/1988 |
| EP | 0650279 A1 | 4/1995 |
| EP | 0792077 A1 | 8/1997 |
| EP | 0838768 A2 | 4/1998 |
| EP | 0853287 A2 | 7/1998 |
| EP | 0908832 A2 | 4/1999 |
| EP | 0918423 A2 | 5/1999 |
| EP | 98118755 | 5/1999 |
| EP | 1014619 A1 | 6/2000 |
| EP | 1030505 A2 | 8/2000 |
| EP | 1052825 A1 | 11/2000 |
| EP | 1445910 A2 | 8/2004 |
| EP | 0779759 B1 | 10/2005 |
| ES | 2171565 T3 | 9/2002 |
| FR | 2761837 A1 | 10/1998 |
| GB | 2282936 A | 4/1995 |
| JP | 5204797 A | 8/1993 |
| JP | H06149689 A | 5/1994 |
| JP | 7183896 A | 7/1995 |
| JP | H085394 A | 1/1996 |
| JP | H08251056 A | 9/1996 |
| JP | 8340308 A | 12/1996 |
| JP | H096798 A | 1/1997 |
| JP | H09130861 A | 5/1997 |
| JP | H09166450 A | 6/1997 |
| JP | H09184878 A | 7/1997 |
| JP | 3300262 B2 | 7/2002 |
| JP | 4431152 B2 | 3/2010 |
| JP | 4615629 B2 | 1/2011 |
| JP | 11085891 A | 4/2011 |
| NL | 1011358 C2 | 8/2000 |
| NL | 1011787 C2 | 10/2000 |
| WO | 9530882 A2 | 11/1995 |
| WO | 9532595 A1 | 11/1995 |
| WO | 9629663 A1 | 9/1996 |
| WO | 9629835 A1 | 9/1996 |
| WO | 9714244 A1 | 4/1997 |
| WO | 9718635 A2 | 5/1997 |
| WO | 9720281 A1 | 6/1997 |
| WO | 9726724 A2 | 7/1997 |
| WO | 9726750 A1 | 7/1997 |

(56) References Cited

FOREIGN PATENT DOCUMENTS

| WO | 9728736 | A1 | 8/1997 |
|---|---|---|---|
| WO | 9806033 | A1 | 2/1998 |
| WO | 9808055 | A1 | 2/1998 |
| WO | 9843150 | A2 | 10/1998 |
| WO | 98/57474 | A1 | 12/1998 |
| WO | 9857474 | A1 | 12/1998 |
| WO | 9859487 | A1 | 12/1998 |
| WO | 99/18532 | A1 | 4/1999 |
| WO | 9918532 | A1 | 4/1999 |
| WO | 9933253 | A1 | 7/1999 |
| WO | 9938313 | A1 | 7/1999 |
| WO | 0050844 | A1 | 8/2000 |
| WO | 0070858 | A1 | 11/2000 |
| WO | 0052921 | A2 | 9/2002 |

OTHER PUBLICATIONS

Nokia, "Nokia 9000 Technical Specifications", Internet Document.
Demmelhuber, "Daten ubers Handy", Funkschau Aug. 1996, pp. 28-35.
"Die fast totale Kommunikation", Elektronik Sep. 1996, p. 30.
Ghneim, "Embedded Web Servers Promise to Change the way we live and work", The Star, Sep. 4, 1997, pp. 1-3.
Press release of WIND RIVER Systems, Inc. "Wind River introduces complete embedded internet package", posted online on Jun. 23, 1997, at http://web.archive.org/web/19971024063125/http://www.wrs.com/embedweb/, pp. 1-3.
Quinnell, "Web servers in embedded systems enhance user interaction", EDN electrical design news, Apr. 10, 1997, pp. 1-6.
Kennedy, "MobileWebTM Changing the face of mobile networking through universal wireless connectivity", IEEE Technical Applications Conference, Nov. 4-6, 1996, pp. 89-94.
Sah et. al., "Programming the Internet from the Server-Side with Tcl and Audience1", The USENIX Fourth Annual Tcl/Tk Workshop, Jul. 1996, pp. 1-5.
Sarkar et. al.,"Internet and relational databases in a multi-tier client/server model", IMA Preprints Series #1439, Institute for Mathematics and its Applications, University of Minnesota, Nov. 9, 1996, pp. 1-22.
Pavlopoulos et. al.,""Ambulance"—mobile unit for health care provision via telematics support", 18th Annual International Conference of the IEEE Engineering in Medicine and Biology Society, Oct. 31-Nov. 3, 1996, pp. 1232-1233.
Johnson, "Ubiquitous mobile host internetworking", Workstation Operating Systems, School of Computer Science, Carnegie Mellon University 1993, pp. 85-90.
Bukhres, "Mobile computing in military ambulatory care", Computer-Based Medical Systems, 1997, Jun. 11-13, 1997, pp. 58-63.
Gessler et. al.,"PDAs as mobile WWW browsers", Computer Networks and ISDN Systems, vol. 28, Issues 1-2, Dec. 1995, pp. 53-59.
Stedman, "Mobile workers can view intranet data while off the network", Computerworld, vol. 30, Issue 35, Aug. 26, 1996, pp. 12.
Jacobs et. al., "IBM deepens NC commitment", Computerworld, vol. 31, Issue 29, Jul. 21, 1997, pp. 1-116.
Kiniry et. al., "A hands-on look at Java mobile agents", Internet Computing, IEEE, Jul.-Aug. 1997, pp. 21-30.
Fonfrocken, "How to Integrate Mobile Agents Into Web Servers," Proceedings of the Sixth IEEE Workshops on Enabling Technologies: Infrastructure for Collaborative Enterprises, 1997, pp. 94-99.
Wu et. al., "Internet access for personal mobile equipments in a wireless WAN environment", Consumer Electronics, vol. 43 , Issue 3, 1997, pp. 873-878.
Makino et al., "Development of Navigation System for the Blind Using GPS and Mobile Phone Combination." 18th Annual International Conference of the IEEE Engineering in Medicine and Biology Society, Nov. 1996, pp. 506-507.
"Financial Focus—Unwired Planet." Interactive Home, Sep. 1, 1996, pp. 1.

Machrone, "Help! My Cell Phone Has a Browsed!", PC Magazine, May 27, 1997, pp. 1-2.
Sullivan, "Net to Help With In-Flight Emergencies", PC Week, Apr. 21, 1997, pp. 1-2.
"Online Help for In-Flight Illness", The Sunday Times, Aug. 10, 1997, pp. 1.
Krage, "The TravTek Driver Information System", IEEE Vehicle Navigation and Information Systems Conference, Oct. 1991, pp. 739-752.
Stewart, "Vehicle Location and Position Monitoring System Using Satellite Navigation and Cellular Telephone." IEEE Colloquium on Vehicle Location and Fleet Management Systems, Jun. 1993, pp. 1-15.
"Web Phones", BYTE, vol. 21, No. 8, Aug. 1, 1996, pp. 1.
Arnaut, "Will Your Next Computer Be a Phone?", The Globe and Mail, Sep. 9, 1997, pp. 1-3.
ITU, "Series T: Terminals for Telematic Services", ITU-T Recommendation T.124, Jan. 2007, pp. 1-208.
ITU, "Visual telephone systems and equipment for local area networks which provide a non-guaranteed quality of service", ITU-T Recommendation H.323, Nov. 1996, pp. 1-81.
Schulzrinne, "Simple Conference Invitation Protocol", Internet Engineering Task Force, Internal Draft, Feb. 22, 1996, pp. 1-19.
Schilit et. al., "TeleWeb: Loosely connected access to the World Wide Web", Computer Networks and ISDN Systems 28 (1996), pp. 1431-1444.
Nokia, "User's Manual", Nokia User's Guides Terms and Conditions, Jun. 7, 1998, pp. 1-126.
Wilson, "The challenge of embedded Internet", Electronic Product Design, vol. 19, Issue 1, Jan. 1998, pp. 31-32, 34.
"NEC to license microserver from spyglass", Nov. 12, 1997, pp. 1-5.
Gonzalez, "CellPort Labs' Technology Lets Autos Act as Web Sites.(Originated from Daily Camera, Boulder, Colo.)", Knight Ridder/Tribune Business News, McClatchy-Tribune Information Services, Mar. 12, 1996.
Liljeberg et al., "Enhaned Services for World-Wide Web in Mobile WAN Environment", Report C-1996-28, Department of Computer Science, University of Helsinki, Apr. 1996, pp. 1-12.
Cooper et al, "PDA Web Browsers: Implementation Issues", Computing Laboratory, The University of Kent of Canterbury, Nov. 9, 1995.
Temme, "The whys and why nots of designing a CDPD modem", Electronic Design, vol. 45, No. 1, Jan. 6, 1997, pp. 122,124,126.
Hoshi et al., "A mobile pen-based computing system for cellular telephone networks", 1993, pp. 380-384.
Kirste, "An infrastructure for mobile information systems based on a fragmented object model", Distributed Systems Engineering, vol. 2, No. 3, Sep. 1995, pp. 161-170.
Kruger, "Growing pains [GSM and Internet technologies]", Communications International, Vo1.24, No. 5, May 1997, pp. 49-50, 52.
Liljeberg et al., "Mowgli WWW software: improved usability of WWW in mobile WAN environments", IEEE Globecom, Communications: The Key to Global Prosperity, 1996, pp. 33-37.
Kojo et al., "An efficient transport service for slow wireless telephone links", IEEE Journal on Selected Areas in Communications, vol. 15, No. 7, Sep. 1997, pp. 1337-1348.
Alanko et al., "Mowgli: improvements for Internet applications using slow wireless links", Proceedings of 8th International Symposium on Personal, Indoor and Mobile Radio Communications—PIMRC, Sep. 1-4, 1997.
Eneroth, "ATM transport in cellular networks", ISS'97: World Telecommunications Congress, Global Network Evolution: Convergence or Collision?, 1997, Proceedings Part vol. 2, pp. 139-146.
Lehmann, "Mobil ins Internet", Funkschau 13/97.
Schooler et al., "An Architecture for Multimedia Connection Management", ISI Reprint Series, ISI/RS 92 294, Aug. 1992, Proceedings IEEE 4th Comsoc International Workshop on Multimedia Communications, MM 1992, pp. 1-6.
Wikipedia, "H.323", Dec. 21, 2010, retrieved from webpage http://en.wikipedia.org/wiki/H.323, pp. 1-14.

(56) References Cited

OTHER PUBLICATIONS

Schulzrinne, "Personal Mobility for Multimedia Services in the Internet", IDMS'96 (European Workshop on Interactive Distributed Multimedia Systems and Services), Mar. 4-6, 1996, pp. 1-18.
Handley et al. "SIP: Session Initiation Protocol", Internet Engineering Task Force, Jul. 31, 1997, pp. 1-66.
"Booklet of the Nokia mobile phone Nokia 9000", Sep. 1996.
Randall, "PROMISE—a personal mobile traveller and traffic information service", IEE Colloquium on Commercialising the Internet, 1997, pp. 1-4.
Gambon, "Wireless web access—Software links smart phones to the Internet", InformationWeek, Jul. 15, 1996, pp. 1-33.

\* cited by examiner

MOBILE TELEPHONE FOR INTERNET APPLICATIONS

This application is a continuation application of and claims priority to co-pending U.S. application Ser. No. 14/622,187, filed Feb. 13, 2015, which is a continuation of U.S. application Ser. No. 12/851,780, filed Aug. 6, 2010, and issued as U.S. Pat. No. 8,995,316, which is a continuation of U.S. application Ser. No. 11/411,263, filed Apr. 26, 2006, which is a divisional of U.S. application Ser. No. 10/309,544, filed Dec. 4, 2004, and issued as U.S. Pat. No. 7,061,897, which is a continuation of U.S. application Ser. No. 09/172,547, filed Oct. 14, 1998, and issued as U.S. Pat. No. 6,519,241, which claims priority to German application No. 197 45 539.5, filed Oct. 15, 1997, there entireties of which are incorporated by reference herein.

The invention relates to a mobile telephone which can be used in particular in a communications system for monitoring and/or guiding a vehicle or for monitoring the medical condition of a patient.

BRIEF DESCRIPTION OF RELATED DEVELOPMENTS

Communications systems for, for example, monitoring and/or guiding a vehicle are generally known. Thus; there are, for example, already vehicles (Internet cars) which are coupled to the Internet, which provides the driver of the vehicle with a whole series of technically interesting possibilities. A disadvantage of such vehicles is, however, that a vehicle computer which has an Internet facility and which is programmed as a standalone WEB server and which is connected to the Internet via a cordless mobile telephone has to be present in the interior of the vehicle. However, such vehicle computers with an Internet facility require a very large amount of space, on the one hand, and are relatively expensive, on the other hand.

SUMMARY OF THE EXEMPLARY EMBODIMENTS

The object of the invention is to develop a mobile telephone of the type mentioned at the beginning in such a way that it makes it possible to communicate on the Internet in a simpler way.

In one embodiment a control unit for a mobile telephone includes a Web server adapted to connect to a Web browser in the mobile telephone, wherein the Web server receives information and provides the information to the Web browser when connected to the Web browser. Other embodiments are directed to a mobile telephone that includes such a control unit and a communications system with a mobile telephone that includes the control unit.

The invention is characterized by the fact that the control unit includes at least one WEB server. A WEB server is in this case a software packet which makes available specific information via an interface to the Internet, which information can be interrogated on request by other devices connected to the Internet. By virtue of the fact that the WEB server is contained in a control unit in a mobile telephone, a locally independent WEB server is easily formed, said server being situated with the user of the mobile telephone at all times if the user carries the telephone with him.

As an alternative, the WEB server can also supply the information via an interface to a local network (LAN) or another network. Furthermore, it is conceivable that a plurality of WEB servers are contained in a mobile telephone, in which case, a WEB server is connected to the Internet while another WEB server may be connected to a local network. Here, it is also conceivable for the individual WEB servers contained in the mobile telephone to be coupled to one another.

According to one advantageous refinement of the invention, the at least one WEB server is contained in the microprogram control unit (MCU) of the mobile telephone. By virtue of the implementation of the WEB server in the microprogram control unit which is already present in a mobile telephone, the mobile telephone does not need to be expanded with additional components.

If the WEB server for the microprogram control unit of the mobile telephone is too large, the mobile telephone may alternatively also contain a separate microprogram control unit in which the WEB server is contained.

According to a preferred development of the invention, the at least one WEB server can be coupled to at least one further server. As a result, information which is associated in terms of content may be contained on each server, making rapid access to the corresponding information, for example for updating purposes, substantially easier. Here, the further server merely needs to be coupled to the WEB server when required, a constant link also being conceivable as an alternative.

According to a further refinement of the invention, the further server is contained in the mobile telephone, as a result of which it is likewise locally independent. However, the further server may also be one which is arranged outside the mobile telephone.

In addition, it is possible for a plurality of servers also to be contained in the mobile telephone or for a plurality of external servers to be connected to the mobile telephone via an air interface. If a plurality of servers are present, they may be, for example, continuously coupled to one another or may be coupled to one another when required. Using an external server, it is possible, for example, for specific information to be transmitted from a service provider via an air interface to the WEB server contained in the mobile telephone. This is advantageous if the information is so extensive that it is not possible to store this information on the locally independent WEB server for reasons of space.

The difference between the WEB server contained in the mobile telephone and the servers contained in the mobile telephone is that only the WEB server can be coupled to a network (Internet, LAN) via an air interface, for example.

According to another refinement of the invention, the WEB server contained in the mobile telephone can be coupled to at least one client. A client is a software packet which requests information from a server, that is to say a second software packet. A typical example is a database interrogation in which a user calls information from the database server by means of a client program.

According to one development of the invention, the at least one client is contained in the mobile telephone. As a result, the user of the mobile telephone can access the individual local servers via this client and interrogate information.

According to yet another refinement of the invention, the client which is contained in the mobile telephone is designed as a WEB browser as a result of which a user of the mobile telephone can call Internet information via an air interface by means of http.

It is also conceivable for the WEB server contained in the mobile telephone to be capable of being coupled to an external client which is designed for example, as an authorized browser and can call information from the WEB server via the air interface.

According to one preferred embodiment of the invention, the WEB server contained in the mobile telephone can itself operate as a client. As a result, the WEB server can call information from an external server (service provider), it being possible, for example, for the client which is designed as a WEB browser and is contained in the mobile telephone to be used for the access to the service provider. In addition, the WEB server is operated as a client if it calls information from one or more servers which are contained in the mobile telephone or else may be of an external design.

In accordance with one preferred embodiment of the mobile telephone according to the invention, the latter is used in a communications system for monitoring and/or guiding a vehicle. Thus, the vehicle can be supervised and controlled by the driver or by an external control centre in a relatively easy way.

According to another preferred embodiment of the mobile telephone according to the invention, it is used in a communications system for monitoring the medical condition of a patient. As a result, it is possible to request medical data in order to monitor the state of health from a central control centre or from a doctor's practice and to initiate actions which may necessary. As an alternative, the user of the mobile telephone may call the information relating to his state of health by means of the WEB browser located in the telephone.

BRIEF DESCRIPTION OF THE DRAWINGS

The invention is described in more detail below with reference to the appended drawings, in which.

DETAILED DESCRIPTION OF THE EXEMPLARY EMBODIMENTS

Figure 1:
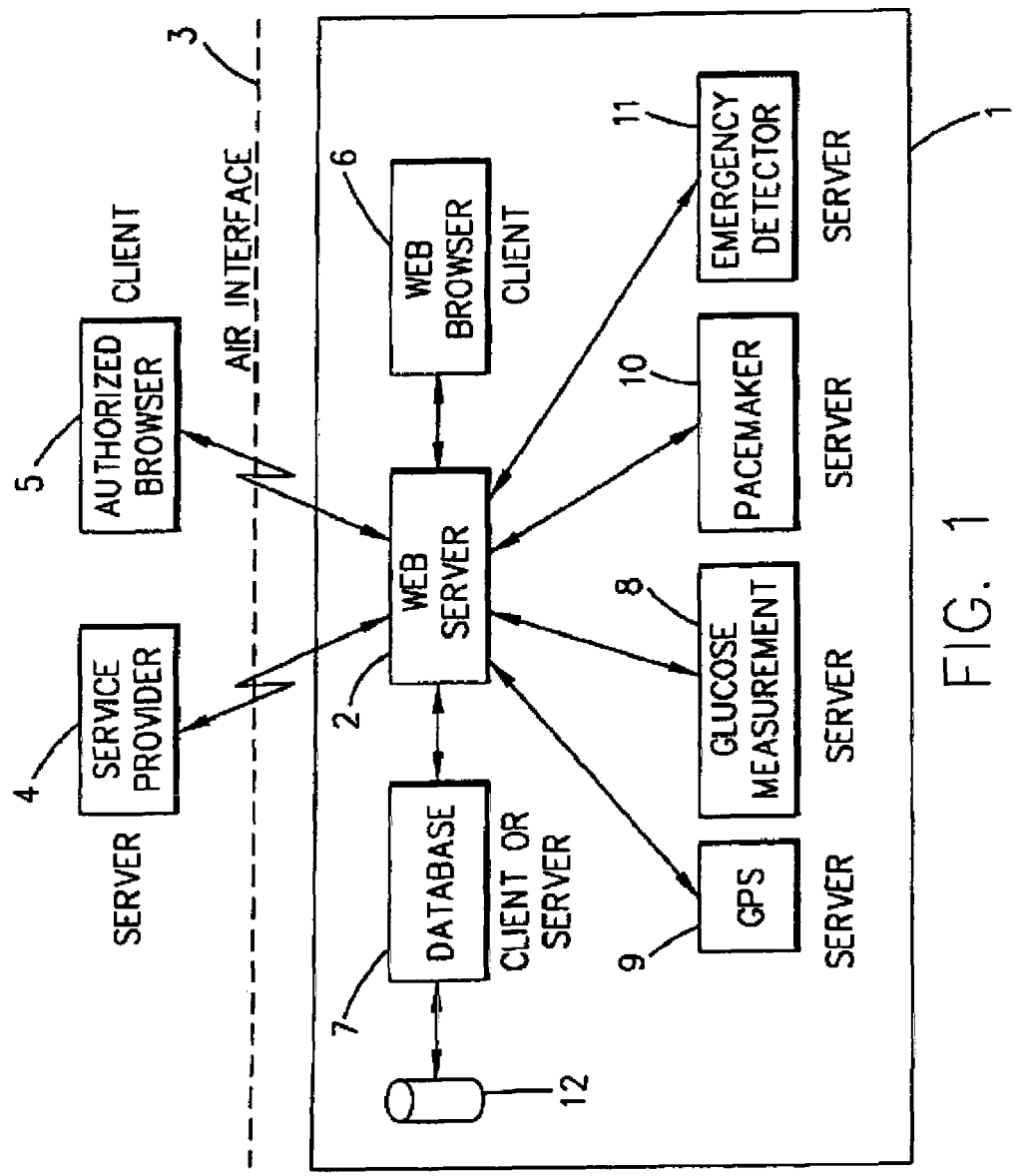
FIG. 1 shows a block diagram of a communications system for monitoring a patient in which the mobile telephone according to the invention is used.

FIG. 1 shows a block diagram of a communications system in which the mobile telephone according to the invention (not shown) is used, in order to monitor a patient medically, the block 1 shown in FIG. 1 being contained in the mobile telephone.

The mobile telephone consequently contains a WEB server 2 which can be coupled via an air interface 3 to a service provider 4 which serves as the server. Furthermore, the WEB server 2 can be coupled via the air interface 3 to an authorised browser 5 which is designed as a client. The external service provider 4 and the external authorized browser 5 are accordingly coupled to the mobile telephone via the radio network, the data communication taking place via the WEB server 2 which is contained in the mobile telephone and which either passes on enquiries of a mobile browser 6 to the outside or receives and evaluates enquiries from the outside. For the purpose of evaluation, a local database 7 is used, which in this case functions as a server. Conversely, the database 7 may also be a client, in which case, in order to update its data stock, devices (for example a glucose measuring sensor) which are connected are called via the WEB browser 2. The WEB browser 6 and local database 7 are likewise situated in the mobile telephone.

The data which are measured by the glucose measuring sensor are transmitted to a glucose measuring server 8 contained in the mobile telephone, and are stored there. Thus, a medical service computer (authorised browser 5) may periodically interrogate the medical measured values (glucose concentration here) via the WEB server 2 and in the case of emergencies send back instructions. However, in the case of acute emergencies (for example deficit of sugar) which is also possible to request help automatically or manually via the mobile WEB browser 6. For the purpose of targeted guidance in an emergency, a service computer can interrogate the location of the patient who is in difficulties by means of the authorized browser 5 which proves its access authorization by a password or a digital signature, and via the WEB server 2 of a GPS server 9 contained in the mobile telephone.

The mobile telephone also contains a pacemaker server 10 which contains information on the working range of the pacemaker.

Furthermore, the mobile telephone contains an emergency detector server 11 which, for example via an acceleration sensor, receives information indicating whether the patient has fallen. This information can be called at any time via the WEB server 2, in which case, in an emergency, the WEB server 2 can request help automatically using the air interface 3 via the WEB browser 6.

In order to evaluate the information contained in the GPS server 9, glucose measuring server 8, pacemaker server 10 and emergency detector server 11, said information is transmitted via the WEB server 2 to the database 7 which is coupled to a further storage medium 12. The database 7 can consequently be operated as a client or server.

Figure 2:
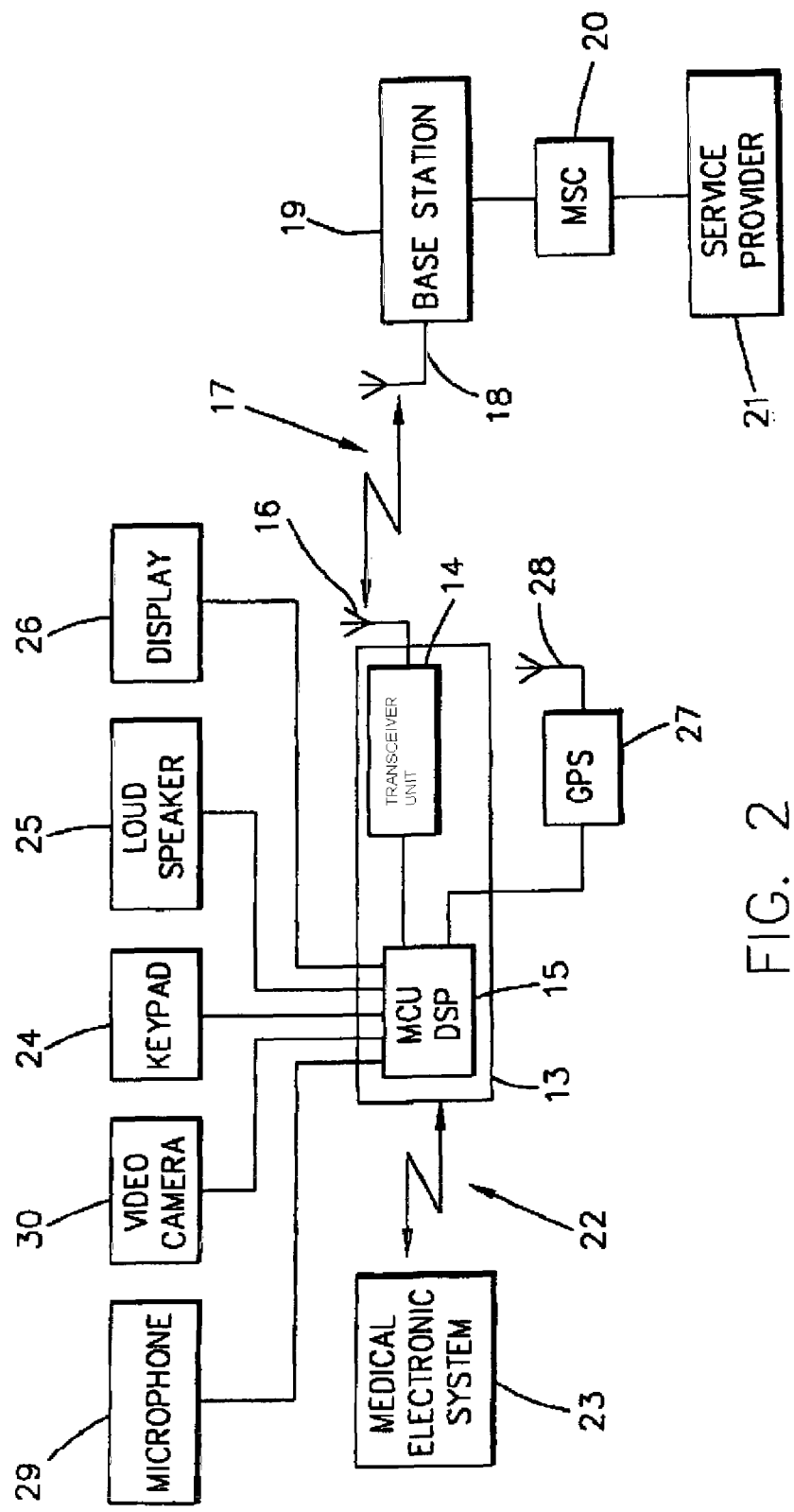
FIG. 2 shows a block diagram of the implementation of the communications system according to FIG. 1.

FIG. 2 shows a block diagram of the implementation of the medical communications system according to FIG. 1.

The WEB server and WEB browser are standard applications which merely have to be tailored somewhat for the concrete applications. All the other servers may be realized as C/C++ programmes which can access the hardware (for example glucose measuring device or the GPS receiver). They are connected to the WEB server via a CGI (common gateway interface). With relatively large data sets it is advisable, owing to the better efficiency, to use the POST access method. In this case the gateway server communicates with the WEB browser via standard input and output.

Because these parts of the system are not visible from the outside, they can easily be replaced by other technologies (for example JAVA or VRML). There is provision for data to be stored in RAM or FLASH as a replacement for the hard disc which can be used only to a limited degree in mobile applications.

In the block diagram according to FIG. 2 there is a mobile telephone 13 in which there are a transceiver unit 14 and a microprogram control unit 15 (MCU) with a DSP.

The block 1 which is shown in FIG. 1 is, in the case of the communications system for the medical monitoring of a patient, contained completely in the microprogram control unit 15 of the mobile telephone 13 according to the invention.

By way of a first antenna 16, the mobile telephone 13 is coupled using the transceiver unit 14 and an air interface 17 to a base station 19 containing an antenna 18. The base station 19 can, for example, be contained in a GSM system and be coupled to a service provider 21 via a mobile switching centre (MSC) 20.

The mobile telephone 13 is also coupled via an interface 22 to a medical electronic system 23. This medical electronic system 23 contains a glucose measuring sensor for determining the glucose concentration of a person with diabetes or some other metabolic illness which influences the balance of sugar. The glucose concentration can be measured automatically here, the results being transmitted to the mobile telephone 13 via the interface 22. The transfer is preferably effected in a wireless fashion (for example via a low-power and short-range RF transmission) in order to avoid the need for a permanent mechanical link between the measurement device and mobile telephone. In the event of an interruption in the transmission of data, the measurement device should store values together with their time of production. Alternatively, instead of the periodic automatic measurement by appropriate sensor electronics, the blood sugar values may also be entered regularly by the person with diabetes into the mobile terminal via a keypad 24.

The medical electronic system 23 also contains a pacemaker with a radio transceiver module. As soon as problematic working ranges of the pacemaker are detected (for example permanent overloading owing to exceptionally high physical activity or technical problems of the device), a message is transmitted via the interface 22 to the mobile telephone 13 located in the vicinity, and is fed via the WEB server 2 from FIG. 1 to the local database 7 and stored there. As already described above, in the event of the detection of a problematic working range of the pacemaker, the WEB browser 6 contained in the MCU 15 of the mobile telephone 13 can be started automatically, in which case, for example, an audible warning message may be output via a loudspeaker 25 or a visual warning message may be output via a display 26. Alternatively, a warning message may also be transmitted to the service provider 21 via the interface 17, the base station 19 and the MSC 20.

The medical electronics system also contains an automatic help request facility which can be triggered, for example, via an acceleration sensor which detects a fall or accident. A further technically simple solution consists in the patient registering periodically at a service point per WEB browser. If the message is not received, a voice link is set up to the patient to ask for information. If the patient does not reply, the service centre initiates a help action owing to the possible emergency. The external authorized browser 5 from FIG. 1 can make an enquiry via the WEB server of the telephone and interrogate the precise location of the person, possibly from a GPS receiver 27. The GPS receiver 27 may likewise be integrated in the mobile telephone 13 here, in which case it receives the GPS satellite signals via a second antenna 28.

The mobile telephone 13 additionally contains a microphone 29 and a video camera 30. Using the microphone, a patient who has, for example, fallen may request help if he is no longer capable of operating the key pad 24. The microphone 29 may be, for example, operated automatically if the abovementioned acceleration sensor triggers a help request.

Using the video camera 30, a remote diagnosis of a patient may be carried out, in which case the doctor attending can also obtain a visual impression of the patient.

Figure 3:
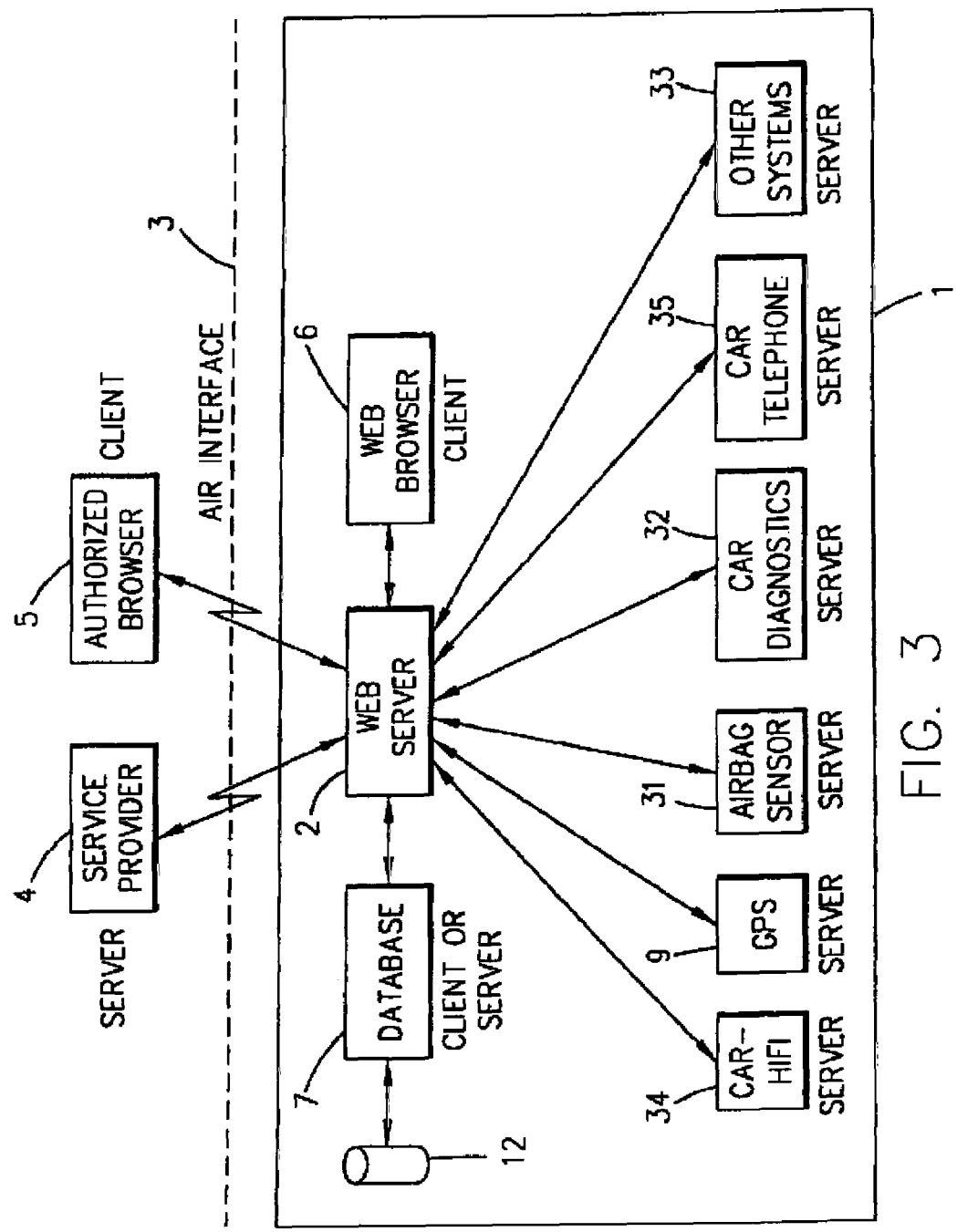
FIG. 3 shows a block diagram of a communications system, for monitoring and/or guiding a vehicle in which the mobile telephone according to the invention is used.

FIG. 3 shows a block diagram of a communications system for monitoring and/or guiding a vehicle in which the mobile telephone according to the invention is used, in which case the same reference symbols as in FIGS. 1 and 2 are used for identical components.

For vehicle applications, the same system from FIGS. 1 and 2 can be used with few modifications. The date link to medical equipment must merely be replaced here by interfaces to the vehicle electronics system and other built-in devices.

FIG. 3 shows a block 1 which is contained in a mobile telephone (for example in the MCU of the mobile telephone) and has a WEB server 2 which is coupled to a WEB browser 6 which is designed as a client.

The communications system which is shown in FIG. 3 can, for example, be used for vehicle navigation. For this purpose, a user requests a route planning operation from a service provider 4 via the WEB browser 6 by entering the destination and the peripheral conditions. The request is then locationed in a queue of a database server 7. The database client 7 then processes requests by requesting from a GPS server 9 the current location and the current safety status from an airbag server 21 and from a diagnostic server 32. This information is then sent to the service provider 4. In response, the driver receives a local road map to the destination, on which map the optimum route is marked. The WEB browser 6 then periodically interrogates the database server 7 in order to output on a screen (not shown in FIG. 3) visual information for the current location and/or to direct the driver through audible messages which are appropriate for the situation. The database client 7 remains active in the background and follows the GPS location of the driver. When the location of the vehicle reaches the boundaries of the local map, the client automatically sends a request to the service provider 4 to update the local map. Between two such requests an external data link is not necessary since all the knowledge for the local route planning operation is located in the vehicle.

The database client 7 monitors the safety status of the vehicle by periodically sending enquiries to the GPS server 9, the airbag server 31 and the diagnostic server 32, in order to detect critical situations. If an accident or other serious disruptions occur, the database client 7 automatically transmits an emergency call to the service provider. The latter replies with a description of the associated action to be initiated by it and opens a voice channel to the driver. In this way, if appropriate, enquiries can, if appropriate, be made regarding the health status of the occupants of the vehicle, or a help action can be effectively planned.

FIG. 3 also shows an authorized browser 5 which is designed as a client and via which a central transport data base (not shown), implemented at a forwarding agent's, has access to the entire vehicle fleet. If a fleet management application is active in the vehicle, the local database client 7 periodically transmits the GPS location, destination, status and cargo of the vehicle to the central database server which stores this information.

The communications system shown in FIG. 3 can also be used for protection against theft and for chasing vehicles, in which case the protection against theft should be initiated by the owner of the vehicle by transmitting an authorization key to the service provider 4. If anyone enters the vehicle without permission, the local database client 7 is started automatically and periodically interrogates the current location from the GPS server 9 and transmits an alarm message with the location to the service provider 4. The latter can then deactivate the vehicle by intervening in the engine electronics. Alternatively, the location can be reported to the police authorities.

The question regarding the technical state of a vehicle or its maintenance can be answered by interrogating the car-diagnostic server 32 which has access to the relevant technical systems in the car. The diagnostic date could be evaluated after the information has been requested in a locally connected service computer by means of the WEB browser 6. Otherwise, this information can be interrogated by the authorized external WEB browser 5 and evaluated at a service point (for example motor vehicle workshop). An expert at a remote location can use the latter procedure to evaluate the faults in the vehicle.

As is shown in FIG. 3, the block 1 also contains a server 33 for other systems. This server can be used, for example, for monitoring vehicle devices such as the heater, for example. The monitoring is carried out here by means of the local WEB browser 6 or else using the external authorized browser 5. This enables the vehicle heater to be actuated from home or from the workplace.

The WEB server 2 is also coupled to a car HIFI server on which, for example, compressed audio information is stored. In mobile radios of the third generation (UMTS, successor of GSM) a considerably larger dataset can be transmitted. This makes it possible to offer personally tailored Internet Radio and Video Services if the tariffs for this are attractive and there is a simple automatic payment registration system. A user tunes into an Internet channel by means of push technology (i.e. he receives the current information of the channel, for example a radio station, without requesting it). Alternatively a user can make contact with his private WEB server in order to transfer his desired programme (for example a compressed audio CD). The received data may be compressed audio information, MIDI music or compressed video information. This information can be called by the user via the WEB browser 6 and the WEB server 2, as a result of which the mobile Internet terminal replaces a radio and a portable television.

FIG. 3 also shows a car telephone server 35 which is contained in block 1 and which is coupled to the WEB server 2, and which can be accessed via the WEB browser 6 or via the authorized browser 5.

Figure 4:
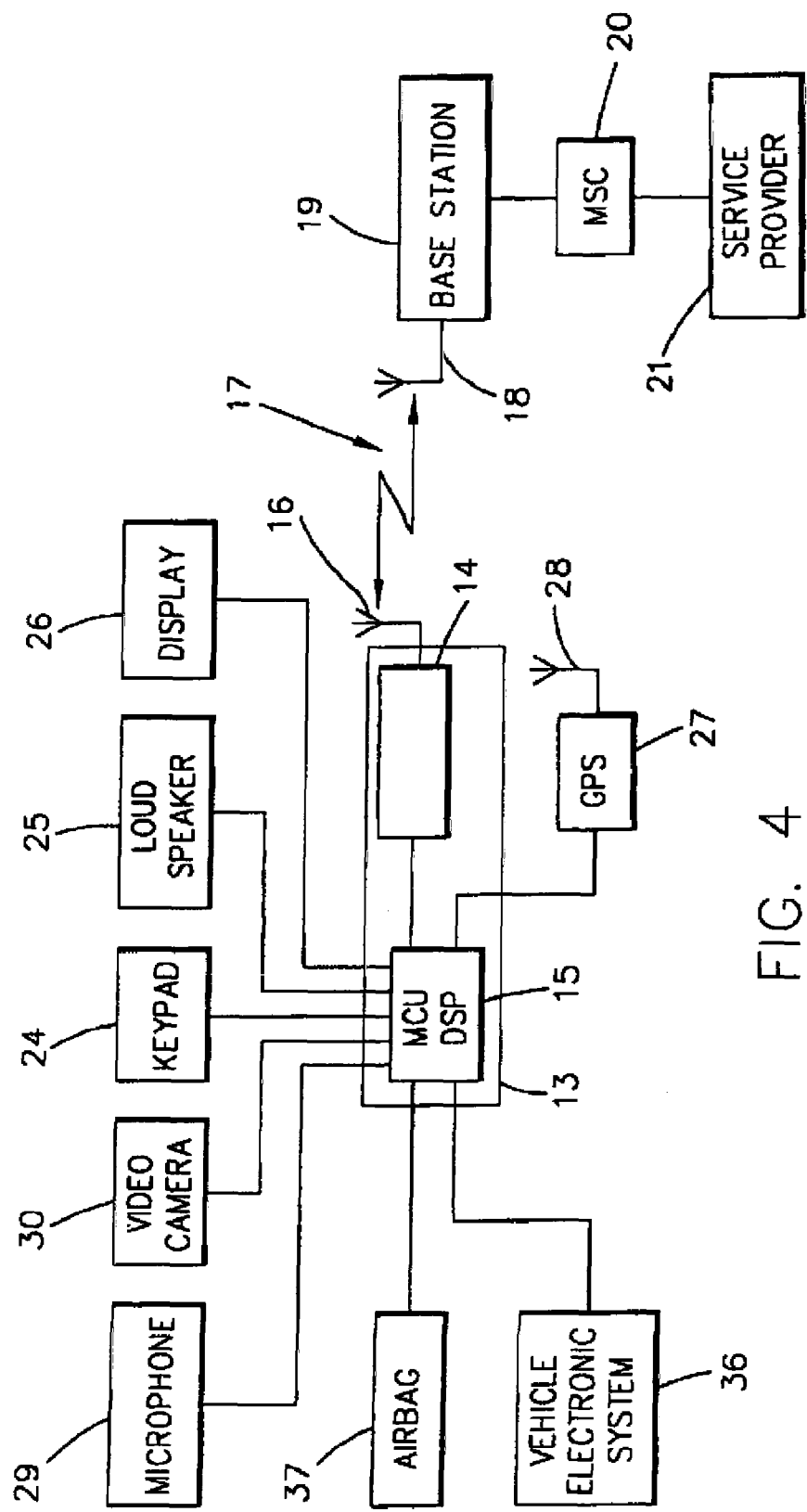
FIG. 4 shows a block diagram of the implementation of the communications system according to FIG. 3.

FIG. 4 shows a block diagram of the implementation of the communications system according to FIG. 3, identical reference numerals to those in FIG. 2 being used for identical components.

FIG. 2 and FIG. 4 differ only in that the mobile telephone 13 in FIG. 4 is coupled to a vehicle electronic system 36 and to an airbag sensor 37 (in a dedicated way or via an air interface) instead of to a medical electronic system.

The airbag sensor 37 continuously supplies signals to the airbag sensor server 31 from FIG. 3, in which case in the event of an accident the database client 7 from FIG. 3 which continuously interrogates the airbag sensor server 31 automatically transmits an emergency call to the service provider 21 via the air interface 17.

The vehicle electronic system 36 also continuously transmits data to the car diagnostic server 32 from FIG. 3. As already described above, this car diagnostic server 32 can be accessed when necessary, it being also possible to intervene in the vehicle electronics system via the authorized browser 5.

What is claimed is:

1. A mobile telephone comprising:
    at least one processor; and
    at least one memory including computer program code for one or more programs,
    the at least one memory and the computer program code configured to, with the at least one processor, cause the mobile telephone to perform at least the following,
    execute a web server in the mobile telephone for internet applications; and
    execute a web browser in the mobile telephone that is configured to utilize first information,
    wherein the web server in the mobile telephone is configured to facilitate a providing of the first information,
    wherein the first information comprises information based on data obtained by the mobile telephone via an air interface for cellular communications from a service provider external to the mobile telephone;
    wherein the mobile telephone is further configured to transmit via the air interface second information in response to receipt by the mobile telephone of a request from an external client via the air interface for the second information, wherein the web server is configured to facilitate providing the second information; and
    wherein the mobile telephone further comprises a GPS system, the GPS system comprising a GPS receiver and an antenna for receiving GPS satellite signals.

2. The mobile telephone of claim 1, wherein one or more servers in the mobile telephone, including a GPS server, are connected to the web server via a common gateway interface.

3. The mobile telephone of claim 1, wherein the mobile telephone comprises more than one server, and wherein the more than one server are configured to interact with each other.

4. The mobile telephone of claim 1, wherein the first information comprises location-related information.

5. The mobile telephone of claim 1, wherein the second information comprises a location of a user of the mobile telephone.

6. The mobile telephone of claim 1, wherein the second information comprises a location of the mobile telephone.

7. The mobile telephone of claim 1, wherein the second information comprises location information based on data from the GPS system of the mobile telephone.

8. The mobile telephone of claim 1, wherein the web browser in the mobile telephone is connected to the web server in the mobile telephone.

9. The mobile telephone of claim 1, wherein the web browser is configured to receive third information from the web server; wherein the third information is based on information obtained by the web server from a further server in the mobile telephone; and wherein the first information, the second information, and the third information comprise location-related information.

10. The mobile telephone of claim 1, wherein the mobile telephone is configured for guiding and monitoring a vehicle.

11. The mobile telephone of claim 1, wherein the mobile telephone is configured for monitoring a medical condition of a patient.

12. An apparatus comprising:
    at least one processor; and
    at least one memory including computer program code for one or more programs,
    the at least one memory and the computer program code configured to, with the at least one processor, cause the apparatus to perform at least the following,
    execute a web server in a mobile telephone for internet applications; and execute a web browser in the mobile telephone that is configured to utilize first information, wherein the web server in the mobile telephone is configured to facilitate a providing of the first information, wherein the first information comprises information based on data obtained by the mobile telephone via an air interface for cellular communications from a service provider external to the mobile telephone;

wherein the mobile telephone is further configured to transmit via the air interface second information in response to receipt by the mobile telephone of a request from an external client via the air interface for the second information, wherein the web server is configured to facilitate providing the second information; and wherein the mobile telephone further comprises a GPS system, the GPS system comprising a GPS receiver and an antenna for receiving GPS satellite signals.

13. The apparatus of claim 12, wherein one or more servers in the mobile telephone, including a GPS server, are connected to the web server via a common gateway interface.

14. The apparatus of claim 12, wherein the mobile telephone comprises more than one server, and wherein the more than one server are configured to interact with each other.

15. The apparatus of claim 12, wherein the first information comprises location-related information.

16. The apparatus of claim 12, wherein the second information comprises a location of a user of the mobile telephone.

17. The apparatus of claim 12, wherein the second information comprises a location of the mobile telephone.

18. The apparatus of claim 12, wherein the second information comprises location information based on data from the GPS system of the mobile telephone.

19. The apparatus of claim 12, wherein the web browser in the mobile telephone is connected to the web server in the mobile telephone.

20. The apparatus of claim 12, wherein the web browser is configured to receive third information from the web server; wherein the third information is based on information obtained by the web server from a further server in the mobile telephone; and wherein the first information, the second information, and the third information comprise location-related information.

21. The apparatus of claim 12, wherein the mobile telephone is configured for guiding and monitoring a vehicle.

22. The apparatus of claim 12, wherein the mobile telephone is configured for monitoring a medical condition of a patient.

* * * * *